United States Patent [19]

Lewis et al.

[11] 4,375,673
[45] Mar. 1, 1983

[54] CHARGE SPECTROGRAPH

[75] Inventors: Richard B. Lewis, Williamson; Richard F. Koehler, Jr., Webster; Edward W. Connors, Rochester, all of N.Y.

[73] Assignee: Xerox Corporation, Stamford, Conn.

[21] Appl. No.: 186,981

[22] Filed: Sep. 15, 1980

[51] Int. Cl.³ ............................................. G06F 15/36
[52] U.S. Cl. ................................ 364/555; 250/396 R; 356/335
[58] Field of Search ................. 364/554, 555; 356/300, 356/302, 303, 326, 335; 250/274, 315.2, 396 R, 397, 472, 473

[56] References Cited

U.S. PATENT DOCUMENTS

| | | | |
|---|---|---|---|
| 2,537,628 | 1/1951 | Hanson et al. | 364/555 X |
| 3,208,286 | 9/1965 | Richard | 364/555 X |
| 3,723,712 | 3/1973 | Komline, Sr. et al. | 364/555 X |
| 3,944,797 | 3/1976 | Coulter et al. | 364/555 |

OTHER PUBLICATIONS

T. Gillespie et al., "An Instrument for Determining the Electric Charge Distribution in Aerosols", *Canadian Jour. of Chemistry*, vol. 30, 12-1952, pp. 1056-1068.

W. J. Megan et al., "Electric Mobility of Sub-Micron Particles", *Nature*, vol. 219, Jul. 20, 1968, pp. 259-261.

B. Liu et al., "Study of The Electric Charge Carried by Spherical Polystyrene Latex particles, Suspended in Air", *C. R. Acadamie of Science of Paris*, Series B, Jun. 23, 1969, pp. 1682-1685.

*Primary Examiner*—Jerry Smith

[57] ABSTRACT

An apparatus in which the distribution of tones particles is measured as a function of the size and charge thereof. The toner particles pass through a uniform electrical field in the interior chamber of the housing. The resultant deflection from a reference is a function of the size and charge of the particle. A computer driven image analysis system displays a toner charge distribution.

21 Claims, 10 Drawing Figures

CHARGE SPECTROGRAPH

This invention relates generally to electrophotographic printing, and more particularly concerns an improved apparatus for measuring the charge distribution of toner particles used in the developer material of an electrophotographic printing machine.

In electrophotographic printing, a photoconductive member is charged to sensitize the surface thereof. The charged photoconductive member is exposed to a light image of an original document being reproduced. Exposure of the sensitized photoconductive surface discharges the charge selectively. This records an electrostatic latent image on the photoconductive surface corresponding to the informational areas contained within the original document being reproduced. Development of the electrostatic latent image recorded on the photoconductive surface is achieved by bringing a developer material into contact therewith. Typical developer materials comprise the heat settable plastic powder, known in the art as toner particles, which adhere triboelectrically to coarser magnetic carrier granules, such as ferromagnetic granules. The toner particles are selected to have the appropriate charge relative to the electrostatic latent image recorded on the photoconductive surface. When the developer material is brought into contact with the latent image recorded on the photoconductive surface, the greater attractive force thereof causes the toner particles to transfer from the carrier granules to the electrostatic latent image.

Frequently, the variability of the electrical characteristics of the developer material introduces undesirable affects on the resultant copy produced in the printing machine. The charging, and charge stability versus environment and use of the toner particles is a significant problem which has persisted throughout the history of electrophotographic printing. Heretofore, most attempts to study the charge condition of particles was constrained to particles having low charges moving in a low velocity air stream. Generally, the particles had a change ranging from about 10 to about $10^3$ electron charges. However, toner particles generally are highly charged, i.e. in the range of from about $10^4$ to about $10^5$ electron charges.

The following art appears to be relevant as to the different types of devices heretofore used to measure low level charges:

Canadian Journal of Chemistry
Volume 30, Page 1056
Author: Gillespie et al.
Published: December, 1952

Nature
Volume 219, Page 259
Author: Megaw et al.
Published: July 20, 1968

C.R. Academie of Science of Paris
Series B, Page 1682
Author: Liu et al.
Published: June 23, 1969

The pertinent portions of the foregoing articles may be summarized briefly as follows:

Gillespie et al. discloses an instrument for measuring low level particle charges. A thin aerosol of particles surrounded by a sheath of clean air is drawn through a transverse electric field between two microscope slides. A low, laminar air flow is used.

Megaw et al. describes charge measurements made in low charge sub-micron spherical polystyrene particles. The apparatus includes a rectangular box having opposite faces made aluminum covered with copper foil. The aluminum plates are insulated from one another. Filter air flowing at a low rate passes around the aerosol of particles.

Liu et al. discloses a spectrometer for studying the charge on polystyrene latex particles. An aerosol of particles is introduced into a tube by a probe. The probe is positioned an equal distance from a pair of parallel plates connected to a voltage source. A flow of filtered air is introduced to maintain a laminar system. Filter paper is positioned in the tube at the end opposed to the probe. In normal operation, the filter paper is replaced by a device insuring the homogenization of the air exiting the tube. Particle concentration is measured by a meter.

In accordance with the features of the present invention, there is provided an apparatus for measuring the distribution of toner particles as a function of the size and charge thereof. The apparatus includes a housing defining an interior chamber with means being provided for producing a laminar air flow having substantially uniform velocity therein. Means form a substantially uniform electrical field in the interior chamber of the housing with means being provided for introducing the toner particles therein. Means receive the particles that have moved through at least a portion of the electrical field in the interior chamber of the housing. Means scan the toner particles deposited on the receiving means to form a display of the particles as a function of the size and charge thereof.

Other aspects of the present invention will become apparent as the following description proceeds and upon reference to the drawings, in which.

While the present invention will hereinafter be described in connection with a preferred embodiment thereof, it will be understood that it is not intended to limit the invention to that embodiment. On the contrary, it is intended to cover all alternatives, modifications and equivalents as may be included within the spirit and scope of the invention as defined by the appended claims.

Figures 1, 9:
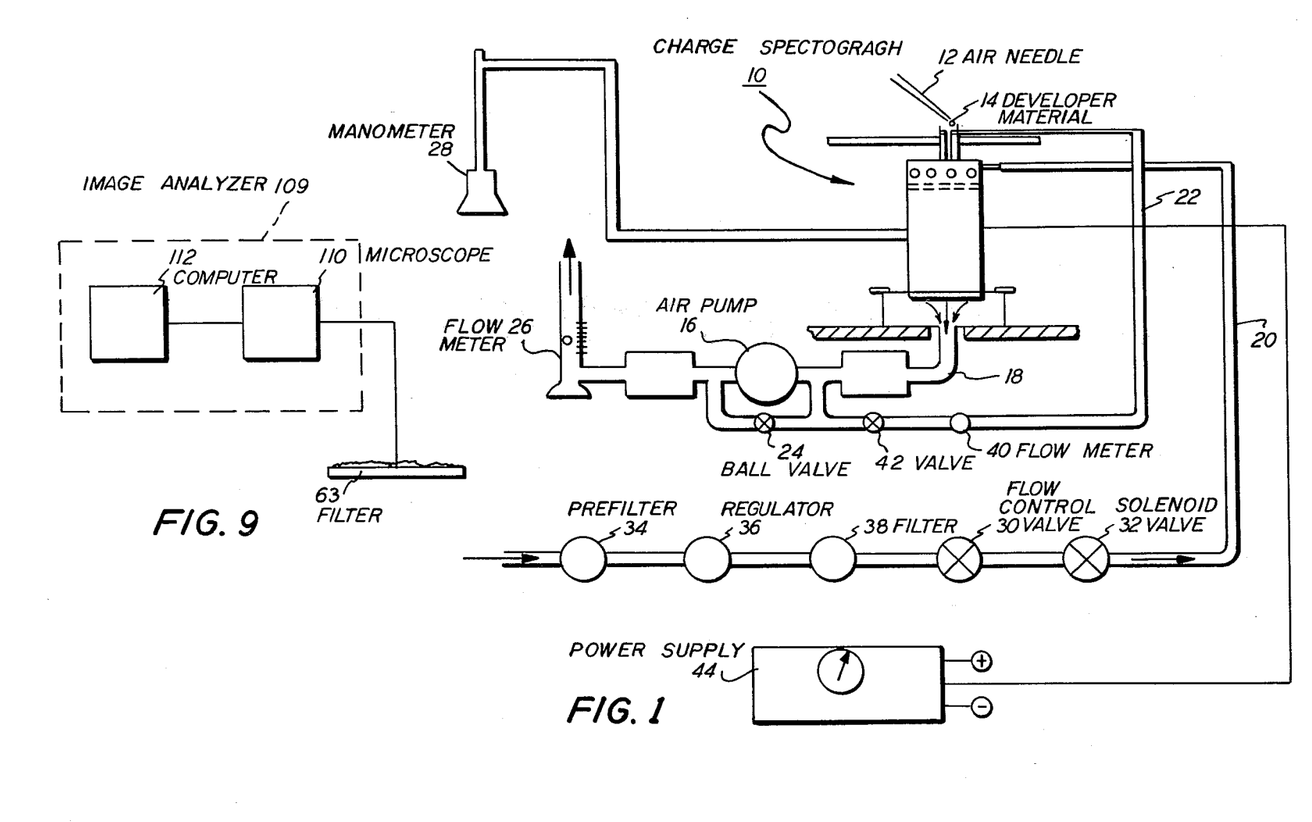
FIG. 1 is a schematic elevational view depicting the system for measuring the charge distribution of toner particles.
FIG. 9 is a block diagram of the system for analyzing the toner particle distribution produced in the FIG. 2 spectrograph.

For a general understanding of the features of the present invention, reference is made to the drawings. In the drawings, like reference numerals have been used throughout to designate identical elements. FIG. 1 schematically depicts the various components of the system for measuring the charge distribution of toner particles. It will become evident from the following discussion that the system described hereinafter is equally well suited for use in measuring the charge distribution of a wide variety of particles and is not necessarily limited in its application to the particular embodiment shown herein.

As shown in FIG. 1, the system includes a charge spectrograph, indicated generally by the reference numeral 10. Air needle 12 directs an air stream onto developer material 14 so as to separate the toner particles from the carrier granules thereof. The toner particles descend into charge spectrograph 10. The system is activated by turning on air pump 16. The system operates at a fixed air velocity of about one meter per second. The main air flow passes through conduit 18. The air flow from the inlet air guard passes through conduit 20, and the exhaust air flow passes through conduit 22. Valve 24, which is a ball type of valve, sets the flow at one meter per second. This flow rate is measured by flow meter 26. Manometer 28 is coupled to interior chamber of charge spectrograph 10 so as to monitor the pressure thereof. This pressure is determined by the design of interior chamber of spectrograph 10. The pressure sets the air velocity level in the interior of spectrograph 10. By way of example, the interior chamber pressure ranges from about 5½ inches to about 6½ inches of water. Valve 30 controls the flow to the inlet air guard. The flow is regulated to be about 180 cubic centimeters per minute. Solenoid valve 32 gates the air flow from the air guard on and off with the main spectrograph switch. The air line for the air guard flow includes a prefilter 34, a regulator 35 which sets the line pressure at 10 psi, and a 5 micron filter 38. Flow meter 40 measures the exhaust air flow from the inlet portion of spectrograph 10. Valve 42 sets this air flow to be about six liters per minute. This setting controls the air volume ratio of sample to clean air surrounding the sample air in the inlet tube. Power supply 44 is coupled to the electrodes of spectrograph 10 and generates an electrical field having an upper limit of 1000 volts per centimeter. Most samples have a field setting of between 20 and 200 volts per centimeter. Power supply 44 is capable of producing from 0 to 6000 volts D.C..

Figure 2:
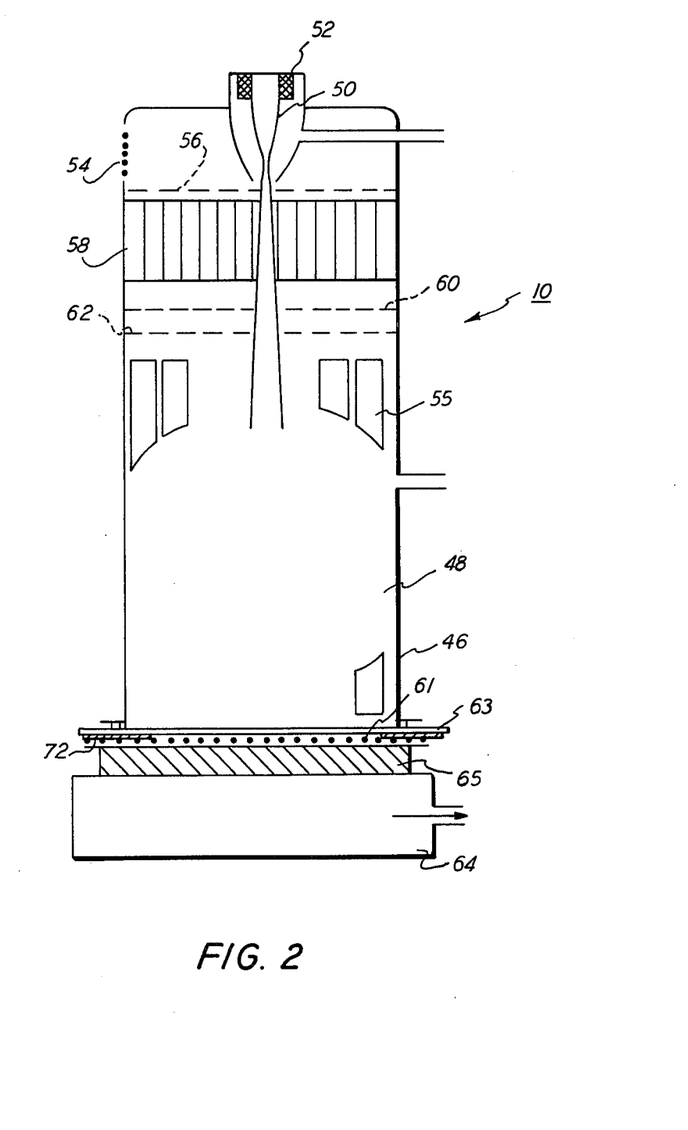
FIG. 2 is a schematic elevational view illustrating the charge spectrograph used in the FIG. 1 system.

Turning now to FIG. 2, there is shown the detailed structure of charge spectrograph 10. Charge spectrograph 10 includes a housing 46 defining an interior chamber of 48. The top section of spectrograph 10 includes inlet tube 50. An annular fine glass frit 52 is positioned about the input portion of tube 50 which places a coaxial air sheath around the entering sample of toner particles. Tube 50 is smooth and made of a drawn-down glass tube. It has a tin oxide coated on its inner surface to provide electrical shielding at a controlled level of potential. The main air flow enters through a nylon screen 54 over an input port. After entering the interior chamber 48 of housing 46, the main air flow passes through a nylon mesh screen 56 and then through a honeycomb flow straightener 58. The main air flow then passes through nylon screens 60 and 62 which have substantially equally sized apertures therein. These nylon screens flatten the air velocity profile so that the velocity of the air flowing across interior chamber 48 of housing 46 is substantially uniform. The conductances of the inlet tube and main air screens and meshes are adjusted so that velocity matching occurs at the outlet of tube 50. Thus, the air flow in the interior chamber 48 of housing 48 is substantially at the same velocity as that of the air flow exiting tube 50. The velocity of the air is approximately 100 centimeters per second. The deflection portion of interior chamber 48 includes electrical field shaping electrodes 55 disposed on the inner walls of housing 46. These electrodes are made from a conductive tin oxide coating on the glass wall of housing 46. The electrodes are a series of substantially rectangular members with their longitudinal axis being substantially parallel to the longitudinal axis of spectrograph 10. Each electrode is set at a different potential so as to produce a uniform field in the interior chamber 48 of housing 46. The outlet portion of tube 50 is positioned within side wall electrode structure 56 and tube 50 is an electrical shield held at ground potential. The base section contains an air permeable grid electrode structure 61 which provides a very smooth potential ramp directly beneath filter 63. It is necessary to have a very smooth ramp in order to avoid distorting the pattern of the particles deposited on filter 63. Electrode 61 is formed from a plurality of substantially equally spaced wires forming one axis of a grid and substantially equally spaced nylon threads forming the other axis of the grid. A plurality of dropping resistors couple the metal wires to power supply 44. Both side wall electrodes 55 and bottom electrodes 61 are driven from a common, ground-center power supply 44. This arrangement generates an electrical field of up to 1000 volts per centimeter. Resistors of bottom electrode 61 are formed by coating one edge of the screen with a slurry of colloidal graphite and molybenium disulfide to form painted on resistors having a resistance of about 20 meg/ohms end to end. Base electrode 61 is supported by a coarse glass frit filter and air field flattener 65. Glass frit filter 65 is mounted on base 64 which is coupled to conduit 18. As toner particles are collected on filter 63, the fields above the toner particles tend to repel subsequent toner particles. In order to minimize the range of these fields above filter 63, it is necessary to make filters 63 slightly conductive. The conductivity must be held sufficiently low so that the filter does not electrically short circuit grid 61. Filter 63 is coated with an electrically conductive liquid, and dried. Thus, in operation, the toner particles descend through inlet tube 50 into the interior 48 of housing 46 where the charge thereon operates in conjunction with the electrical fields established by electrodes 55 and 61 produce a deflection from the nominal vertical. The toner particles are received in filter 63 with the zero input corresponding to the center line of inlet tube 50. Deviations from this zero point or center line are a function of the size and charge of the toner particle.

Figure 3:
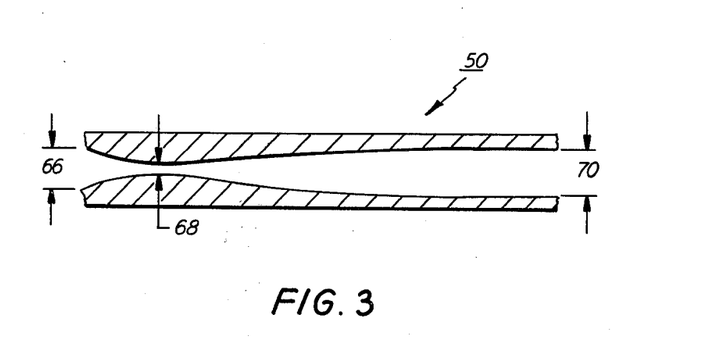
FIG. 3 is a fragmentary sectional view showing the inlet tube of the FIG. 2 spectrograph.

Referring now to FIG. 3, there is shown inlet tube 50 in greater detail. As shown thereat, inlet tube 50 is designed to minimize the possibility of toner particles hitting the interior walls or from being trapped. To shape the required venturi to achieve this, tube 50 is made preferably from glass having a tin oxide coating thereon which is electrically grounded or at zero potential. The inlet portion, indicated generally by the reference numeral 66, is approximately 2.0 millimeters in diameter. The width of the orifice 68 or the throat region is approximately 0.4 millimeters in diameters. The outlet portion, indicated by the reference numeral 70, is approximately 2.2 millimeters in diameter. The volume of air flowing through inlet tube 50 ranges from about 210 to about 260 cubic centimeters per minute.

Figure 4:
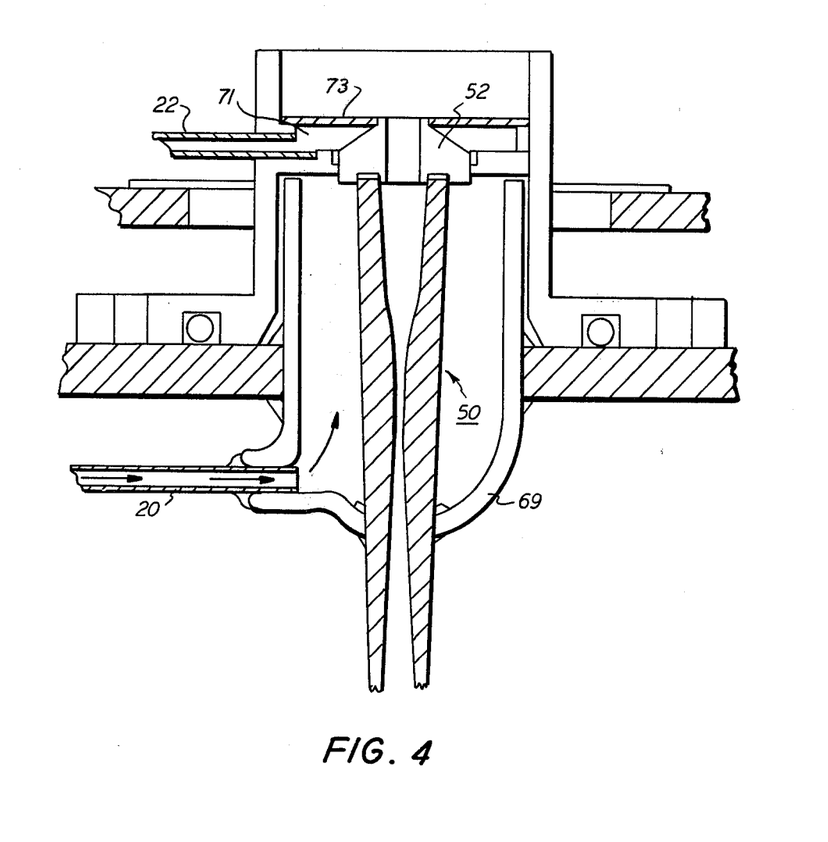
FIG. 4 is a fragmentary elevational view, partially in section, depicting the upper portion of the FIG. 2 spectrograph.

The assembly of subcomponents of charge spectrograph 10 located at the entrance thereof is shown in greater detail in FIG. 4. Referring now to FIG. 4, the air flow through conduit 20 sets the ratio of sample air to guard air. Air enters air shield 69 through conduit 20 at a volume of about 150 to 200 cubic centimeters per minute. This air flow forms a sheath around the sample air entering inlet tube 50 with the volume thereof controlling the sampling rate. If a residual toner cloud were allowed to dwell in the vicinity of the inlet portion of tube 50, the entering sample would be biased in favor of low charged particles. Thus, the toner cloud must be sampled and the residual particles removed from consideration before this can distort the measurement. This is achieved by exhaust duct 71 which sweeps the toner cloud toward the inlet of inlet tube 50. The unused particles are trapped on filter 73 which fits tightly around inlet tube 50. The developer sample is held about 5 to 10 millimeters above inlet tube 50 and the toner particles stopped therefrom.

Figure 5:
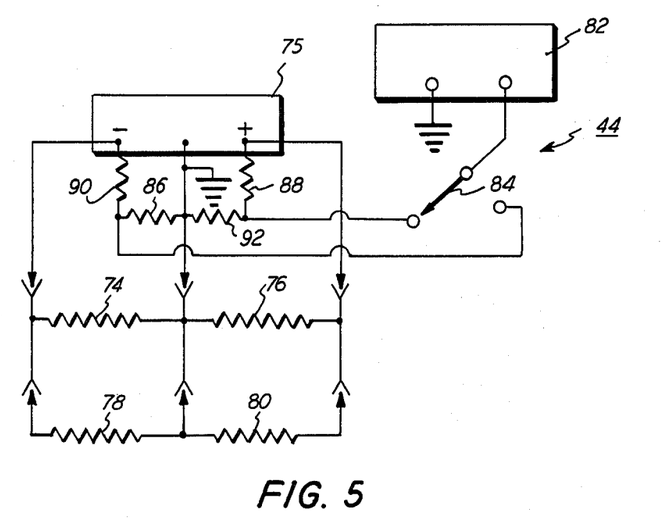
FIG. 5 is a diagram of the circuitry associated with the electrodes used in the FIG. 2 spectrograph.

The electrical field across the deflection chamber of the spectrograph varies the sensitivity thereof. The proper setting will disperse the trace as far as possible within the limits set by the aperture of washer 72 disposed beneath filter 63 (FIG. 2). To obtain accurate reproducable charge data, this field is resettable to an accuracy of approximately 1%. The circuitry of power supply 44 is shown in FIG. 5. A stable adjustable power supply and digital voltmeter are connected to the spectrograph as shown in FIG. 5.

As shown in FIG. 5, painted bottom resistors 74 and 76 are connected to power supply 75. Resistors 74 and 76 have a resistance of approximately 10 megohms. Similarly resistors 78 and 80 are connected to side wall electrodes 56. Resistors 78 and 80 have a resistance of about 3 megohms. Digital voltmeter 82 is coupled by a switch 84 to power supply 75 through resistors 86, 88, 90 and 92. Switch 84 provides a balance check of power supply 75. Preferably, resistor 86 has a resistance of 330 kilohms, resistor 88, a resistance of 660 kilohms, resistor 90, a resistance of 660 kilohms and resistor 92 a resistance of 330 kilohms, so that the meter reads directly in volts per centimeter.

Figure 6:
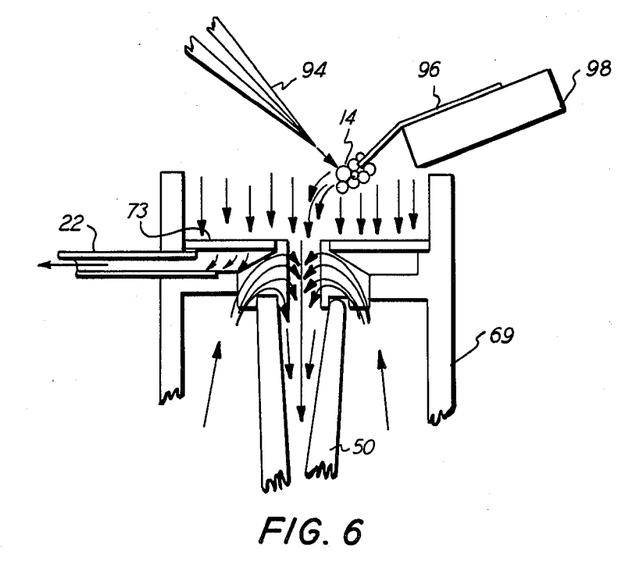
FIG. 6 is a fragmentary elevational view showing toner particles being introduced into the FIG. 2 charge spectrograph.

As shown in FIG. 6, developer sample 14 is held about 5 to 10 millimeters above inlet tube 50. Toner particles are stripped from developer material 14 by air flowing from an air needle 94. Developer material is supported over the edge of the inlet tube and the air needle is directed at the developer material at an angle of about 45° relative to the axis of tube 50. Developer material 14 is attracted magnetically to support 96 which is mounted on a magnetic chuck 98.

Figure 7:
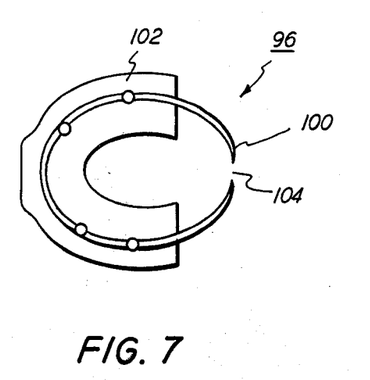
FIG. 7 is a plan view of the device used to support developer material as toner particles are being placed in the FIG. 2 spectrograph.

As shown in FIG. 7, support 96 includes a one millimeter diameter steel wire 100 cemented to a horseshoe magnet 102. Steel wire 100 is cemented to magnet 102. The wire is bent so that the poles formed therein are separated from one another and extend away from magnet 102. Developer material is then held between the poles of steel wire 100 in the vicinity of opening 104.

Figure 8:
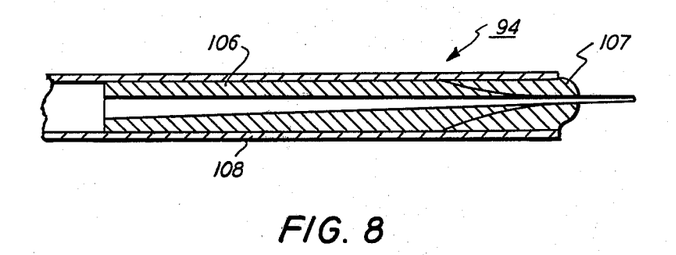
FIG. 8 is an elevational view, partially in section, showing the needle for directing a stream of air onto the developer material to separate the toner particles therefrom so that the toner particles descend into the FIG. 2 spectrograph.

Referring now to FIG. 8, there is shown air needle 94 in greater detail. As depicted thereat, a pyrex glass tube 106 is drawn to form a fine nozzle for the air jet. Cement 107 secures tube 106 to the interior of stainless steel tube 108. A fine, high velocity air stream is then directed at the developer material supported on support 96. Toner particles are completely stripped from the carrier granules of the developer material where the air directly impinges thereon. Air is supplied to air needle 94 at a pressure ranging from 15 to 20 psi and a flow of about 5 cubic centimeters per second for a 100 micron opening in tube 106.

Turning now to FIG. 9, after the toner particles have been collected on filter 63, it is mounted on a computer driven image analyzer 109. Preferably, image analyzer 109 is an Omnicon manufactured by Bausch and Lomb. Image analyzer 109 includes a microscrope 110 having a stage for supporting filter 63 thereon and computer 112. Activation of computer 112 starts an interactive program which controls microscrope 110 and produces an histogram of particle charge distribution. Preferably, computer 112 is a Nova-2 computer. Filter 63 has a pair of zero spots which are made by sampling toner with power supply 75 set at zero volts. These are used as references for the image analysis. The trace is then scanned in a square wave pattern. Data for the total sample is initially printed. This data includes the size distribution of the entire sample independent of charge. A computed triboelectric characteristic of the entire sample and the average charge are also printed. The charge/diameter for each particle is known, in as much as displacement is known, the diameter of each particle is measured and the charge thereof may be readily determined. Thus, the charge distribution for each size particle is printed. A typical histogram is shown in FIG. 10.

Figure 10:
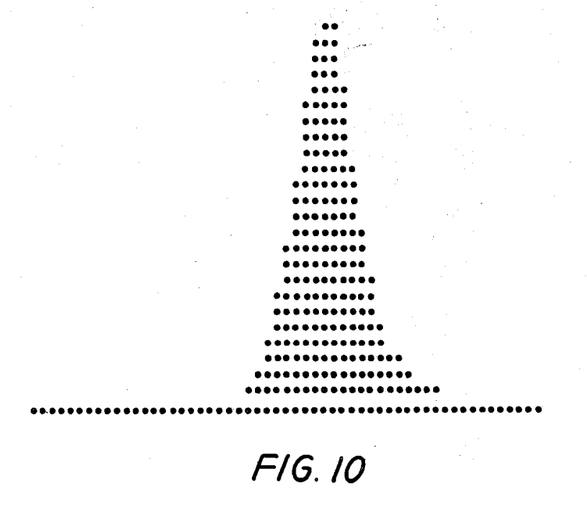
FIG. 10 is a computer generated histogram of a typical toner particle distribution.

Referring now to FIG. 10, the computer terminal produces a histogram of count versus charge divided by diameter rather than charge alone as printed for each size particle. Since each size corresponds to a narrow range in sizes, the histograms can be directly scaled to charge.

The basic program for controlling computer 112 is listed in the Appendix.

In recapitulation, it is clear that a system for measuring the charge distribution of toner particles represents a significant tool for determining satisfactory or unsatisfactory developer material. With the utilization of this tool, developer material may be inspected on a continuous or sampling basis to insure that the material utilized in the electrophotographic printing machine has the requisite charge properties. The apparatus of the present invention produces a printout which provides a measurement of the charge distribution of the toner particles.

It is, therefore, evident that there has been provided, in accordance with the present invention, an apparatus for measuring toner particle charge which fully satisfies the aims and advantages herein before set forth. While this invention has been described in conjunction with a specific embodiment thereof, it is evident that many alternatives, modifications and variations will be apparent to those skilled in the art. Accordingly, it is intended to embrace all such alternatives, modifications, and variations as fall within the spirit and broad scope of the appended claims.

APPENDIX

```
2000  REM        SCAN 2 ---  CHARGE SPECTROGRAPH SCANS 11/11/75
2010  DIM D[33,29],E[33,29],P[30],C[29],U[30],V[30],Q[67]
2020  CALL 75
2025  CALL 70,31,60
2030  CALL 70,32,60
2040  GOSUB 4120
2050  PRINT "FOR OPTIONS, TYPE 1, OTHERWISE 0";
2055  INPUT Q0
2060  IF Q0= 0 GOTO 2080
2062  PRINT "FOR OPTIONS: SELECT=1, REJECT=0"
2064  PRINT "GRAPH OUTLINE     COMPACT PRINTOUT     NO SMOOTHING";
2066  INPUT Q0,U4,U5
2070  LET Q0=Q0+2*U4+4*U5
2075  PRINT
2080  GOSUB 4400
2082  LET D1=1
2084  LET D2=25
2086  LET D3=2
2090  GOSUB 4500
2100  LET T1= 0
2110  LET C1= 0
2120  LET C2= 0
2130  LET P[30]= 0
2140  LET A1= 0
2150  LET A2= 0
2160  LET B1= 0
2170  FOR I1= 0 TO Q6-1
2180     LET D0=D1+D2*(I1+.5)
2190     LET U8= 0
2200     LET P[I1]= 0
2210     LET C[I1]= 0
2220     LET U[I1]= 0
2230     FOR I2= 0 TO 33
2250        IF D[I2,I1]<=P[I1] GOTO 2280
2260        LET P[I1]=D[I2,I1]
2280        IF E[I2,I1]<=P[I1] GOTO 2300
2290        LET P[I1]=E[I2,I1]
2300        LET U8=U8+D[I2,I1]+E[I2,I1]
2310        LET C1=C1+D0*(D[I2,I1]*(I2+Q4)+E[I2,I1]*(I2+34+Q4))
2320        LET C[I1]=C[I1]+D[I2,I1]*(I2+Q4)+E[I2,I1]*(I2+34+Q4)
2330        LET U[I1]=U[I1]+D[I2,I1]*(I2+Q4)*(I2+Q4)
2340        LET U[I1]=U[I1]+E[I2,I1]*(I2+34+Q4)*(I2+34+Q4)
2350     NEXT I2
2360     IF U8<=P[30] GOTO 2380
2370     LET P[30]=U8
2380     LET V[I1]=U8
2390     LET A1=A1+U8*D0
2400     LET A2=A2+U8*D0*D0
2410     LET C2=C2+U8*D0*D0*D0
2420     LET B1=B1+U8*D0*D0*D0*D0
2430     LET T1=T1+U8
2440  NEXT I1
2445  LET V[Q6]= 0
2450  FOR I1= 0 TO 33
2460     LET V[Q6]=V[Q6]+D[I1,Q6]+E[I1,Q6]
2470  NEXT I1
2473  PRINT "<13>"
2475  CALL 71,31
```

```
2476    PRINT
2480    GOSUB  3600
2490    FOR I1= 0 TO Q6
2500      LET Q[I1]=V[I1]
2510    NEXT I1
2520    GOSUB  3800
2530    LET U5=.01*T1
2540    LET U7=P[30]
2550    LET U2=1
2555    LET U3=Q6
2560    GOSUB  4300
2570    LET U4= 0
2580    LET U6=Q6
2590    LET U2=D1+.5*D3
2600    LET U9=D3
2610    GOSUB  5400
2620    PRINT "       DIAMETER   (MICRONS)<13>"
2630    PRINT "TOTAL COUNT =";T1;
2640    PRINT   TAB (25);"TOTAL Q/M = ";17.9813*L2*C1/(E1*C2);"UC/G"
2650    PRINT "AVG D = ";A1/T1;
2660    PRINT   TAB (25);"AVG D**2 = "; SQR (A2/T1)
2670    PRINT "AVG D**3 = ";(C2/T1)^.3333;
2680    PRINT   TAB (25);"AVG D**4 = ";(B1/T1)^.25
2690    PRINT "DVS = ";C2/A2; TAB (25);"DV = ";B1/C2
2700   .PRINT "AVG Q = ";94.15*L2*C1/(10000*E1*T1);"FC<13>"
2710    FOR I1= 0 TO Q6-1
2712      LET U7=P[I1]
2714      IF  INT (Q0/4)-2* INT (Q0/8)=1 GOTO  2758
2718      LET Q[ 0]=.75*D[ 0,I1]+.25*D[1,I1]
2720      LET U3=U[I1]*V[I1]-C[I1]*C[I1]
2722      LET U7=Q[ 0]
2724      LET Q[33]=.25*(D[32,I1]+E[ 0,I1])+.5*D[33,I1]
2726      IF U7>=Q[33] GOTO  2730
2728      LET U7=Q[33]
2730      LET Q[34]=.25*(D[33,I1]+E[1,I1])+.5*E[ 0,I1]
2732      IF U7>=Q[34] GOTO  2736
2734      LET U7=Q[34]
2736      LET Q[67]=.75*E[33,I1]+.25*E[32,I1]
2738      IF U7>=Q[67] GOTO  2742
2740      LET U7=Q[67]
2742      FOR I2=1 TO 32
2744        LET Q[I2]=.25*(D[I2-1,I1]+D[I2+1,I1])+.5*D[I2,I1]
2746        LET Q[I2+34]=.25*(E[I2-1,I1]+E[I2+1,I1])+.5*E[I2,I1]
2748        IF U7>=Q[I2] GOTO  2752
2750        LET U7=Q[I2]
2752        IF U7>=Q[I2+34] GOTO  2756
2754        LET U7=Q[I2+34]
2756      NEXT I2
2757      LET U7= INT (U7+.5)
2758      LET U3=U[I1]*V[I1]-C[I1]*C[I1]
2760      IF U3>= 0 GOTO  2766
2762      LET U3= 0
2764      GOTO  2770
2766      LET U3= SQR (U3)
2770      PRINT "<13>"
2780      CALL 71,S1
2790      PRINT
2810      PRINT "     D = ";D1+D3*(I1+.5);"+<8>_";.5*D3;"MICRONS"
2820      PRINT "  NMAX = ";U7;"<13>   NTOT = ";V[I1]
2840      IF V[I1]<= 0 GOTO  3140
2850      LET U9=94.15*L2/(E1*V[I1]*10000)
2860      PRINT "       AVG Q/D = ";U9*C[I1];"FC/MICRON"
2870      PRINT "   STD DEV Q/D = ";U9*U3;"FC/MICRON<13>"
```

```
2885    IF  INT (Q0/4)-2* INT (Q0/8)= 0 GOTO  2926
2890    FOR I2= 0 TO 33
2900      LET Q[I2]=D[I2,I1]
2910      LET Q[I2+34]=E[I2,I1]
2920    NEXT I2
2924    GOTO 2930
2926    PRINT "    DATA SMOOTHED"
2930    IF  INT (Q0/2)-2* INT (Q0/4)= 0 GOTO  2980
2940    LET U5=10
2970    GOTO 3010
2980    LET U5=.005*V[I1]
2990    IF V[I1]>50 GOTO  3015
3000    LET U5=1+ SGN ( INT (U7/10))*(U7/10-1)
3010    PRINT "  NO NORMALIZATION...   * =";U5;"PARTICLES<13>"
3015    LET U2=1
3020    IF Q0-2* INT (Q0/2)= 0 GOTO  3035
3030    LET U2= 0
3035    LET U3=Q5
3040    GOSUB  4300
3050    LET U4=Q4
3060    LET U6=Q4+Q5
3070    LET U2= 0
3080    LET U9=94.15*L2/(10000*E1)
3090    GOSUB  5400
3100    LET I2=-7
3110    IF Q4<I2 GOTO  3130
3120    LET I2=Q4
3130    PRINT  TAB (-Q4+I2);"Q/D    FC/MICRON"
3140  NEXT I1
3150  PRINT "<13><13>TO SAVE ON TAPE, TYPE 1, OTHERWISE 0";
3170  INPUT U4
3180  IF U4= 0 GOTO  3200
3190  GOSUB  5000
3200  PRINT "TYPE 1 TO DO MORE LINES, 0 TO QUIT";
3210  INPUT U4
3230  IF U4<>1 GOTO  3295
3280  GOSUB  4100
3290  GOTO  2090
3295  STOP
3400  CALL 6,1,18
3405  CALL 3,12,1,1,1000
3410  CALL 4,1,U6,U7
3415  CALL 4, 0,U2,U3
3420  LET U7=1000/U2
3425  LET U6=1000/U6
3430  CALL 6,U6,18
3435  IF D3+U7<1 GOTO  3495
3437  CALL 3,12,1,1,( INT (D1*U7+.5)+.1)/U6
3438  CALL 4,1,U2,U0
3439  IF U0= 0 GOTO  3490
3440  LET U3= INT (D2*U7+.5)
3441  LET U5=U0
3442  FOR I3= 0 TO Q6-1
3443    LET U[I3]= 0
3444  NEXT I3
3445  CALL 3,12,1,1,(U3+.1)/U6
3450  CALL 4,1,U2,U[Q6]
3452  LET U0=U[Q6]
3455  FOR I3=Q6-1 TO  0 STEP -1
3460    LET U2= INT ((D1+D3*I3)*U7+.5)
3465    CALL 3,12,1,1,(U2+.1)/U6
3470    CALL 4,1,U[I3],U1
3475    LET U[I3]= INT ((U1-U0)*D3*U7/(U3-U2)+.5)
```

```
3477     LET U0=U1
3478     IF U0>=U5 GOTO  3490
3480     LET U3=U2
3485   NEXT I3
3490 RETURN
3495 PRINT "SIZE INCREMENTS TOO SMALL FOR THIS OBJECTIVE"
3500 RETURN
3600 LET I3=7
3610 FOR I1= 0 TO Q6-1 STEP 8
3620   IF Q6-I1>7 GOTO  3640
3630   LET I3=Q6-I1-1
3640   FOR I2= 0 TO I3
3650     PRINT  TAB (8*I2);D1+D3*(I1+I2+.5);
3660   NEXT I2
3670   PRINT
3680   FOR I2= 0 TO I3
3690     PRINT  TAB (8*I2);V[I2+I1];
3700   NEXT I2
3710   PRINT "<13>"
3730 NEXT I1
3740 PRINT "NUMBER >";D2;"=";V[Q6]
3750 RETURN
3800 CALL 2,U5,U5,U5,U4
3801 LET U4=15-U4
3802 DEF  FNA(X)= SGN ( ABS (X))
3810 LET U5=59- FNA(U4)*8- FNA(U4-2)*4- FNA(U4-4)- FNA(U4-6)*16
3811 LET U5=U5- FNA(U4-1)*16- FNA(U4-3)*4- FNA(U4-5)*2- FNA(U4-7)*8
3820 PRINT "<13>";2.5*U5;"% OBJECTIVE<13>"
3830 RETURN
4000 LET U6= SGN (U4-X1)* INT ( ABS (U4-X1)/5+.5)
4005 IF  ABS (U6)>=8000 GOTO  4080
4010 IF  ABS (X1/5+U6)>=8000 GOTO  4080
4015 LET U7= SGN (U5-Y1)* INT ( ABS (U5-Y1)/5+.5)
4020 IF  ABS (U7)>=4000 GOTO  4080
4025 IF  ABS (Y1/5+U7)>=4000 GOTO  4080
4030 LET X1=X1+5*U6
4035 LET Y1=Y1+5*U7
4040 CALL 1,-U6,U7
4045 IF Q2>= 0 GOTO  4060
4050 LET X1= 0
4055 LET Y1= 0
4060 IF  ABS (Q2)<>1 GOTO  4085
4065 CALL 2,U6,U6,U7,U6
4070 IF U7=1 GOTO  4065
4075 GOTO  4085
4080 PRINT "MOTION ASKED FOR TOO LARGE.INPUT NEW VALUES."
4085 RETURN
4100 PRINT "THE HEADER IS:"
4110 CALL 71,S1
4120 PRINT "<13>TYPE NEW HEADER (CR TO ACCEPT OLD)";
4130 CALL 72,S2
4140 CALL 73,S2, 0,U4
4150 IF U4= 0 GOTO  4180
4160 CALL 76,S1,S2, 0,58
4170 GOTO  4100
4180 RETURN
4300 FOR U7= INT (U7/U5) TO  0 STEP -1
4305   LET U4= 0
4310   FOR U6= 0 TO U3
4315     IF  ABS (Q[U6]-U5*(U7+1))<=.5*U5 GOTO  4335
4320     IF Q[U6]<U5*(U7+.499) GOTO  4360
4325     IF  INT ((U6-.8)/66)+3*U2<> 0 GOTO  4335
4327     IF Q[U6-1]<U5*(U7+.499) GOTO  4335
```

```
4330        IF Q[U6+1]>=U5*(U7+.499) GOTO  4360
4335        FOR U4=U4 TO U6-1
4340           PRINT " ";
4345        NEXT U4
4350        PRINT "*";
4355        LET U4=U6+1
4360     NEXT U6
4390     PRINT
4395  NEXT U7
4399  RETURN
4400  LET U4= 0
4405  LET U5= 0
4410  LET Q2=-1
4415  LET X1= 0
4420  LET Y1= 0
4425  PRINT "RELEASE STAGE,MOVE TO FIRST ZERO SPOT"
4430  GOSUB  4000
4435  PRINT "INPUT X,Y CO-ORDINATES OF SECOND ZERO SPOT"
4437  LET Q2=1
4440  INPUT U4,U5
4445  LET U4=5* INT (200*U4)
4450  LET U5=5* INT (200*U5)
4455  IF  ABS (U4-X1)+ ABS (U5-Y1)= 0 GOTO 4480
4470  GOSUB  4000
4475  GOTO  4440
4480  PRINT "OFFSET ANGLE = ";57.296* ATN (X1/Y1)
4485  LET Q3=X1/Y1
4490  RETURN
4500  PRINT "INPUT X,Y CO-ORDINATES OF LINE CENTER"
4505  LET Q2=1
4510  INPUT U4,U5
4515  LET U4=5* INT (200*U4)
4520  LET U5=5* INT (200*U5)
4530  IF  ABS (U5-Y1)+ ABS (U4-X1)= 0 GOTO 4545
4535  GOSUB  4000
4540  GOTO  4510
4545  LET Q2=-1
4550  LET U5=(U5+Q3*U4)/(1+Q3*Q3)
4555  LET U4=Q3*U5
4560  LET X2=-U4
4565  LET Y2=-U5
4570  GOSUB  4000
4580  PRINT "INPUT X CO-ORDINATE OF LEFT END OF LINE"
4585  LET Q2=1
4590  INPUT U4
4595  LET U4=5* INT (200*U4)
4600  IF U4-X1= 0 GOTO 4620
4605  LET U5=-U4*Q3
4610  GOSUB  4000
4615  GOTO  4590
4620  PRINT "INPUT LINE WIDTH AND LENGTH IN MM";
4625  INPUT W1,L1
4630  PRINT "INPUT E-FIELD IN V/CM";
4635  INPUT E1
4640  PRINT "D MIN=";D1;" D MAX=";D2;" D STEP=";D3
4645  PRINT "TYPE KEY FOR SIZES:STANDARD(1), NEW(-1), PRESENT(0)";
4650  INPUT U4
4660  IF U4= 0 GOTO 4700
4665  IF U4> 0 GOTO 4685
4670  PRINT "INPUT D MIN, D MAX, D STEP";
4675  INPUT D1,D2,D3
4680  GOTO 4700
4685  LET D1=1
```

```
4690  LET D2=25
4695  LET D3=2
4700  IF (D2-D1)* ABS (D3) <= 0 GOTO  4715
4705  LET O6= INT ((D2-D1)/D3+.9)
4707  LET D2=D1+O6*D3
4710  IF O6<30 GOTO  4725
4715  PRINT "TOO MANY SIZES REQUESTED OR D1>D2"
4720  GOTO  4670
4725  LET W1=1000*W1
4730  CALL 3,10,1, 0, 0
4735  CALL 4, 0,L2,W2
4740  CALL 3,11,1, 0, 0
4745  CALL 4, 0,W2,U4
4750  LET L2=L2/W2
4755  LET W2=1.05*W2
4760  LET Q4= INT (X1/L2)
4765  LET L1=1000*L1
4770  LET Q5= INT (L1/L2+1)
4775  IF Q5<68 GOTO  4810
4780  LET Q5=67
4785  PRINT "MAXIMUM LINE:";68*L2/1000;"MM"
4790  PRINT "TO RESET LINE, TYPE 1, OTHERWISE 0";
4795  INPUT U4
4800  IF U4<> 0 GOTO  4580
4810  FOR I1= 0 TO 33
4815     LET Q[I1]= 0
4820     LET Q[I1+34]= 0
4825     FOR I2= 0 TO 29
4830        LET D[I1,I2]= 0
4835        LET E[I1,I2]= 0
4840     NEXT I2
4845  NEXT I1
4850  LET C1=1
4855  FOR I1= 0 TO Q5
4860     FOR I2=-C1* INT (W1/W2) TO C1* INT (W1/W2) STEP 2*C1
4865        LET U4=L2*(I1+Q4)
4870        LET U5=-U4*Q3+I2*W2/2
4875        GOSUB  4000
4880        GOSUB  3400
4885        CALL 5, 0,U4/1000,U0
4888        IF U0= 0 GOTO  4920
4890        FOR I3= 0 TO Q6
4895           IF I1>33 GOTO  4910
4900           LET D[I1,I3]=D[I1,I3]+U[I3]
4905           GOTO 4915
4910           LET E[I1-34,I3]=E[I1-34,I3]+U[I3]
4915        NEXT I3
4920     NEXT I2
4925     LET C1=-C1
4930  NEXT I1
4935  LET U4=X2
4940  LET U5=Y2
4945  LET Q2=-2
4950  GOSUB  4000
4955  CALL 3, 0,1, 0, 0
4960  CALL 5, 0, 0, 0
4965  CALL 4, 0,U4,U4
4970  LET Q2=1
4975  RETURN
5000  PRINT "<16>0 (PRINTER OFF IDLE 0)"
5010  PRINT " (RECORD ON DC2)    <18>"
5020  CALL 71,S1
```

```
5025    PRINT
5060    PRINT "E = ";E1
5070    PRINT "WIDTH = ";L2
5080    PRINT "NUMBER OF SCANS =";Q5+1
5090    PRINT "START AT I = ";Q4
5100    PRINT "MIN D,MAX D,STEP D: ";D1;D2;D3
5110    FOR I1= 0 TO Q5
5120      PRINT I1+Q4
5130      LET U4=9
5140      FOR I2= 0 TO Q6 STEP 10
5150        IF Q6-I2>9 GOTO 5170
5160        LET U4=Q6-I2
5170        IF I1>33 GOTO 5220
5180        FOR I3= 0 TO U4
5190          PRINT D[I1,I2+I3];
5200        NEXT I3
5210        GOTO 5250
5220        FOR I3= 0 TO U4
5230          PRINT E[I1-34,I2+I3];
5240        NEXT I3
5250        PRINT
5260      NEXT I2
5270    NEXT I1
5280    PRINT "<27>F  -  END OF FILE<13>END OF FILE<7>"
5285    PRINT "<19><13><20>  (PLAYBACK OFF, RECORD OFF D3,D4)"
5290    PRINT "(PRINTER ON IDLE 9)  <16>9"
5295    RETURN
5400    FOR U2=U4 TO U6
5410      IF ABS (U2- INT (U2/10)*10)<=.1 GOTO 5440
5420      PRINT ".";
5430      GOTO 5450
5440      PRINT "!";
5450    NEXT U2
5460    PRINT
5470    FOR U2= INT (U4/10+.95) TO INT (U6/10)
5480      LET U1=10*U2+U2+U2
5485      LET U3= 0
5490      IF U1= 0 GOTO 5510
5500      LET U3= INT (.434295* LOG ( ABS (U1)))
5510      LET U3=10*U2- SGN ( ABS (U1))-(1+U3)*(1+ SGN (U3+.5))/2
5520      IF U3>=U4 GOTO 5540
5530      LET U3=U4
5540      PRINT TAB (U3-U4); SGN (U1)*.01* INT ( ABS (100*U1));
5550    NEXT U2
5560    PRINT
5570    RETURN
```

What is claimed is:

1. An apparatus for measuring the distribution of highly charged toner particles as a function of the size and charge thereof, including:
   a housing defining an interior chamber;
   a pump coupled to the interior chamber of said housing to produce a flow of air therethrough;
   a plurality of screens disposed in the interior chamber of said housing with each of said plurality of screens being spaced from one another and having substantially uniform apertures therein to produce a substantially uniform pressure drop thereacross so that the air velocity is substantially uniform across the interior chamber of said housing;
   means for forming a substantially uniform electrical field in the interior chamber of said housing;
   means for introducing the toner particles into the interior chamber of said housing;
   means for receiving the particles that have moved through at least a portion of the electrical field in the interior chamber of said housing; and
   means for scanning said receiving means to form a display of the particles as a function of the charge and size thereof.

2. An apparatus according to claim 1, wherein said scanning means automatically scans said receiving means and automatically forms a display of the particles.

3. An apparatus according to claim 2, further including means for separating the toner particles from a carrier granule to which one of more of said toner particles are attached before being placed in said introducing means.

4. An apparatus according to claim 1 or 2, or 3 wherein said receiving means includes a filter positioned in the interior chamber of said housing in the region of an air outlet.

5. An apparatus according to claim 4, wherein said forming means includes:
   a first electrode disposed about the walls of the chamber of said housing to form a substantially uniform electrical field; and
   a second electrode positioned across the bottom of the chamber of said housing in the region of the air outlet.

6. An apparatus according to claim 5, wherein said introducing means includes an inlet tube extending into the interior chamber of said housing, said inlet tube being configured so that air exits therefrom at substantially the same linear velocity as the air flowing in the interior chamber of said housing with the majority of the particles remaining in the inlet air stream without contacting the walls of said tube.

7. An apparatus according to claim 6, wherein said introducing means includes means for generating a flow of air to remove residual particles from the region of the entrance of said inlet tube.

8. An apparatus according to claim 6, wherein said scanning means includes:
   a microscope in communication with said filter having the toner particles deposited thereon; and
   a computer coupled to said microscope for generating a visual display of the toner particles as a function of the size and charge thereof.

9. An apparatus according to claim 6, further including means for straightening the flow of air in the interior chamber of said housing.

10. An apparatus according to claim 3, in which carrier granules are magnetic, wherein said separating means includes:
    a magnetic member for attracting the carrier granules with the toner particles adhering triboelectrically thereto; and
    means for directing a narrow, high speed jet of air onto the carrier granules to separate the toner particles therefrom and move them into said inlet tube.

11. A method of measuring the distribution of highly charged toner particles as a function of the size and charge thereof, including the steps of:
    producing a laminar air flow having substantially uniform velocity in an interior chamber of a housing by actuating a pump coupled to the interior chamber of the housing and directing the air flow in the chamber of the housing through a plurality of spaced screens having substantially uniform apertures therein to produce a substantially uniform drop thereacross;
    forming a substantially uniform electrical field in the interior chamber of the housing;
    introducing the toner particles into the interior chamber of the housing;
    receiving the toner particles that have moved through at least a portion of the electrical field in the interior chamber of the housing on a support member; and
    scanning the support member to form a display of the toner particles deposited on the support member as a function of the charge and size thereof.

12. A method according to claim 11, wherein said step of scanning includes the step of automatically scanning the support member to automatically form a display of the toner particles deposited on the support member as a function of the charge and size thereof.

13. A method according to claim 12, further including the step of separating the toner particles from carrier granules before said step of introducing the toner particles into the interior chamber of the housing.

14. A method according to claims 11, 12 or 13, wherein said step of scanning includes the steps of:
    placing the support member with the toner particles deposited thereon in communication with a microscope; and
    energizing a computer coupled to the microscope to generate a visual display of the toner particles as a function of the size and charge thereof.

15. A method according to claim 12, wherein said step of introducing includes the step of matching the linear velocity of the air flow in the interior chamber of the housing with the air stream conveying the toner particles therein.

16. A method according to claim 15, wherein said step of introducing includes the step of generating a flow of air to remove residual toner particles from the region of the entrance to the interior chamber of the housing.

17. A method according to claim 16, further including the step of straightening the flow of air in the interior chamber of the housing.

18. An apparatus for measuring the distribution of highly charged toner particles as a function of the size and charge thereof, including:
    a housing defining an interior chamber;
    means for producing a laminar air flow having substantially uniform velocity of approximately one hundred centimeters per second in the interior chamber of said housing;
    means for forming a substantially uniform electrical field in the interior chamber of said housing;
    means for introducing the particles into the interior chamber of said housing;
    means for receiving the particles that have moved through at least a portion of the electrical field in the interior chamber of said housing; and
    means for scanning said receiving means to form a display of the particles as a function of the charge and size thereof.

19. A method of measuring the distribution of highly charged toner particles as a function of the size and charge thereof, including the steps of:
    producing a laminar air flow having substantially uniform velocity of approximately one hundred centimeters per second in an interior chamber of a housing;
    forming a substantially uniform electrical field in the interior chamber of the housing;
    introducing the toner particles into the interior chamber of the housing;
    receiving the toner particles that have moved through at least a portion of the electrical field in the interior chamber of the housing on a support member; and
    scanning the support member to form a display of the toner particles deposited on the support member as a function of the charge and size thereof.

20. An apparatus for measuring the distribution of highly charged toner particles as a function of the size and charge thereof, including:
    a housing defining an interior chamber;
    means for producing a laminar air flow having substantially uniform velocity in the interior chamber of said housing;

means for forming a substantially uniform electrical field in the interior chamber of said housing;

means for introducing the particles into the interior chamber of said housing;

means for receiving the particles that have moved through at least a portion of the electrical field in the interior chamber of said housing, said means for receiving positioned at a portion of said housing to receive all particles including those having no or only slight charges; and means for scanning said receiving means to form a display of the particles as a function of the charge and size thereof.

21. A method of measuring the distribution of highly charged toner particles as a function of the size and charge thereof, including the steps of:

producing a laminar air flow having substantially uniform velocity in an interior chamber of a housing;

forming a substantially uniform electrical field in the interior chamber of the housing;

introducing the toner particles into the interior chamber of the housing;

receiving all toner particles that have moved through at least a portion of the electrical field in the interior chamber of the housing on a support member; and scanning the support member to form a display of the toner particles deposited on the support member as a function of the charge and size thereof.

* * * * *